United States Patent [19]

Robson

[11] Patent Number: 5,231,987

[45] Date of Patent: Aug. 3, 1993

[54] TIME DOMAIN REFLECTOMETER-INTEGRITY TESTING SYSTEM AND METHOD FOR IMPLANTABLE ELECTRODE

[75] Inventor: Jack R. Robson, Beech Grove, Ind.

[73] Assignee: Random Technologies, Inc., Indianapolis, Ind.

[21] Appl. No.: 866,850

[22] Filed: Apr. 10, 1992

[51] Int. Cl.$^5$ ............................................. A61N 1/362
[52] U.S. Cl. ....................................................... 607/29
[58] Field of Search ........................... 128/419, 419 PG

[56] References Cited

U.S. PATENT DOCUMENTS

| | | | |
|---|---|---|---|
| 3,922,914 | 12/1975 | Fuchs | 73/290 R |
| 4,466,288 | 8/1984 | Grynberg et al. | 73/654 |
| 4,786,857 | 11/1988 | Mohr et al. | 324/58.5 X |
| 4,843,234 | 7/1989 | Berthold et al. | 250/227 |
| 4,893,895 | 1/1990 | Berthold et al. | 350/96.29 |
| 4,960,989 | 10/1990 | Liebenrood et al. | 250/227 |
| 5,033,826 | 7/1991 | Kolner | 350/355 |

OTHER PUBLICATIONS

Hewlett Packard. Application Note 62, TDR Fundamentals, Apr. 1988.
Hewlett Packard, Application Note 62-1, Improving Time Domain Network Analysis Measurements, Apr. 1988.
Hewlett Packard, Application Note 62-3, Advanced TDR Techniques, May 1990.
Tektronix/1502C Metallic Time Domain Reflectometer Operator Manual-1st Prn. Mar. 1989—Revised May, 1990.
Genesis TM Cardiac Pacing System-Model 285-Technical Manual Pacesetter Systems, Inc., ©1985—91904-20-001 Rev. N/C.
Ventak® P AICD TM —Model 1600—Physician's Manual Automatic Implantable Cardioverter Defibrillator—1991 Cardiac Pacemakers, Inc.
Quantum TM II—Intermedics TM Cardiac Pulse Generator Physician's Manual Models 253-25 and 254-30—Jan. 1990.
Pacesetter TM Technical Manual—APS-II Model 3000 Programmer With Model 3030 Function Pak 1988.
Cordis Corporation, 1986—Brochure entitled "What do these pacers have in common?".
Tektronix 1502C Metallic Time Domain Reflectometer Service Manual, Tektronix, Inc., 1st Prnt. Jul. 1989—Revised Jul. 1991 pp. 5-1 to 5-11.

*Primary Examiner*—William E. Kamm
*Attorney, Agent, or Firm*—Baker & Daniels

[57] ABSTRACT

A device, system and method is used for testing the integrity of an implantable electrode. The electrical device has a receptacle for an electrode and includes a time domain reflectometer comprising an output signal mechanism operatively connected to the electrode receptacle. The method of analyzing the integrity of an implanted electrode comprises the steps of generating a time domain reflectometer (TDR) reading (output signal) from the electrode, and transmitting the signal to an output device. The output signal may be analyzed to determined whether it varies by a predetermined threshold, or it may be compared to a previously generated signal from the electrode so that differences in the electrical characteristics of the electrode may be identified. The present device, system and method allows a cardiologist or technician to ensure that the electrode is properly implanted and to non-invasively determine the integrity of the electrode over a patient's life.

64 Claims, 5 Drawing Sheets

| NO. | READING DATE | COMMENTS | PHYSICIAN |
|---|---|---|---|
| 1/512 | 01/01/92 | PRE-IMPLANT READINGS W/ TECHTRONICS 1000 | SMITH, J. |
| 2/512 | 01/01/92 | IMPLANTED W/ TECHTRONICS 1000 ELECTRODE | SMITH, J. |
| 3/512 | 02/01/92 | POST-OPERATIVE CHECK-UP | SMITH, J. |
| 4/512 | 07/01/92 | 6 MONTH CHECK-UP OK | JONES, D. |
| 5/512 | 09/15/92 | PATIENT COMPLAINTS OF FATIGUE - CHECKS OK | SMITH, J. |

PRESS ▲ ▼ TO HIGHLIGHT, SELECT TO SELECT

FIG. 3

| ELECTRODE MANUFACTURER | MODEL NO. |
|---|---|
| CARDIAC PACEMAKERS, INC. | CPI 1000 |
| CARDIAC PACEMAKERS, INC. | CPI 1100 |
| INTERMEDICS, INC. | 254-001 |
| INTERMEDICS, INC. | ELECPRO 100 |
| PACESETTER SYSTEMS, INC. | PACE-3000 |

PRESS ▲ ▼ TO HIGHLIGHT, SELECT TO SELECT

FIG. 4

TIME DOMAIN REFLECTOMETER-INTEGRITY TESTING SYSTEM AND METHOD FOR IMPLANTABLE ELECTRODE

FIELD OF THE INVENTION

This invention relates to a device, system and method used in medical testing, and, in particular, to a non-invasive technique for testing the integrity of an electrode implanted within a patient's body.

BACKGROUND OF THE INVENTION

Advances in technology together with an increased understanding of physiological functions has led to the development of a variety of devices which may be implanted into the body to assist or to perform specific functions. Cardiac pacemakers, defibrillators, the Jarvis heart and insulin pumps are just a few examples of these implantable devices. Generally, implantable devices are usually comprised of a power source coupled with electrical and/or mechanical components necessary to perform the desired function. The power source and the other components may require replacement or repair over the life of the patient. Therefore, many implantable devices provide a mechanism for non-invasively providing vital information regarding the device's performance. In this manner, it may be determined without surgery whether the device is in need of repair or replacement or whether the device is approaching a threshold thereby indicating the need for replacement or repair.

A number of cardiac pacemakers available on the market today are capable of being both programmed and evaluated non-invasively. These pacemakers include, for example, the Model 402B Multicor ® II manufactured by Cordis Corporation of Miami, Fla., the Quantum ® Model 254-09 manufactured by Intermedics, Inc. of Freeport, Tex., the Chorus DDD manufactured by ELA Medical, Inc. of Minnetonka, Minn., and the DDD and Genesis ® pacemakers from Pacesetter, Inc. The Ventak ® P Mode 1600 automatic implantable cardioverter defibrillator is another example of an implantable device providing remote programming and evaluation capabilities. These devices typically include an RF transceiver to communicate with an external user interface system, which includes a "programming wand." The external system, such as the Pacesetter ® APS-II Model 3000 Programmer with Model 3030 Function Pack, available from Pacesetter Systems, Inc. of Sylmar Calif., includes controls to allow physician or medical technician program the diagnostic functions of the device and evaluate its operating parameters. The types of information which may be telemetered from, for example, a pacemaker to such an external system include the device's model number, serial number, mode in which the pacemaker is programmed, magnet rate, lead impedance, and electrode/lead information such as the type of electrode implanted in the patient. Also, battery life, one of the vital characteristics affecting the performance of the pacemaker, may also be telemetered. Similarly, defibrillators such as the Ventak ® P AICD ™ Model 1600 manufactured by Cardiac Pacemakers, Inc. of St. Paul, Minn., also are capable of telemetering performance information to such a programming system.

Some types of problems are not readily discernable with the pacemakers and the defibrillators currently available. Specifically, with regard to an electrode connected to such devices, little information, with the exception of type of electrode used, is available through an external programming system. Various types of problems can occur with such electrodes including lead fracture, lead displacement, body reaction to the lead interface, migration of the lead through body tissue, unsatisfactory electrode position and faulty connection with the implantable device. For example, the electrode may be improperly fastened to the pacemaker resulting in an ohmic or loose junction or, after the electrode is implanted, it may rub against a bone within the patient's body and strip the electrode's insulation. Thus, it is desireable to develop an implantable device having an electrode which is capable of providing information about the integrity of the electrode in a non-invasive manner both at the time the device is implanted and throughout the time the electrode remains implanted.

One known method used to attempt to determine the integrity of an implanted electrode is an X-ray radiograph. However, X-ray radiographs are not adequate for integrity testing as they are unable to provide information about the connection between the device and the electrode or the condition of the electrode in a reliable manner. For example, an X-ray radiograph may, in some cases, indicate that a fault is located at the point where the electrode is connected to the pacemaker. However, the performance of other tests or examination of the electrode during a surgical proceeding may reveal a pseudofracture, i.e., no actual fracture is present, such as is caused by the excessive tightening of a suture at that point. Thus, X-ray radiographs can lead to unnecessary surgery intended to correct a non-existent problem. Therefore, it is desireable to determine the integrity of an implanted electrode through the performance of a single, reliable test. Additionally, such a test should not be as susceptible to interpretation or to patient conditions as is X-ray radiography.

Various pacemakers and defibrillators can accommodate various types of electrodes. Generally, there are two types of electrodes. Unipolar electrodes are defined as those in which the anode is the case of the planted device and the cathode is the electrical lead. Bipolar electrodes are those in which the anode is the proximal lead electrode and the cathode is the lead electrode. Examples of bipolar electrodes include the VS1 Bipolar Tined Electrode manufactured by Oscor Medical, Inc. of Palm Harbor, Fla. Some devices such as defibrillators require the utilization of bipolar electrodes so that the defibrillator may deliver shocks to the heart as well as simultaneously monitor the heart's function. Thus, it is desireable to develop an integrity testing system which may be used to test the integrity of both unipolar and bipolar electrodes.

Electrodes for many applications are insulated so as to avoid affecting or being affected by the surrounding tissue. However, the electrodes can deteriorate over time. Thus, it is desirable to develop an integrity testing system for an implanted electrode which is not significantly affected by the natural deterioration of the electrode.

It is also desirable to develop a method for testing the integrity of the electrode which does not interfere with the normal operation of the implanted device. A pacemaker, for example, must send pulses to the heart at a specified rate such as 60 pulses per second. For the pacemaker to continue to operate during the testing procedure, the integrity test must be performed without interfering with those pulses.

Additionally, most implantable devices require little power to operate. Because little power is required to perform the desired function of the device, a battery may be utilized for a lengthy period of time without requiring replacement. Therefore, it is desirable to develop an integrity testing system which does not require significant power to operate so as to avoid reducing the life of the battery used in the device.

Time domain reflectometers, such as the 1502C Metallic Time Domain Reflectometer manufactured by Tektronix, Inc. of Beaverton, Oreg., are used to test the integrity of cable such as co-axial cables. For such integrity testing, time domain reflectometers send electrical pulses down the cable and detect any reflections made by any discontinuities in the cable. Specifically, time domain reflectometers send out successive pulses and measure the respective reflected pulses at times corresponding to points along the cable. Measurements are provided in terms of voltage versus time which can then be converted to resistance over the length of the cable. Time domain reflectometers can locate shorts, opens, defects in the shield of the cable, foreign substances in the cable, kinks, and more. Generally, only one parameter is required for the proper operation of the time domain reflectometer in determining the integrity of a cable. That parameter is the velocity of propagation or the speed of the signal down the cable which varies for different cable dielectric materials. Time domain reflectometers may operate on either a closed or an open circuit. For an open circuit the signal continues to be reflected through the air (or other medium) and returns to the instrument. In general, variations in the resistance measured by the time domain reflectometer indicates a fault such as a bad connection, the stripping of insulation, pressure on the cable, or a break in the cable.

Time domain reflectometry has been used for a variety of applications. In U.S. Pat. No. 4,466,288, time domain reflectometry is used to evaluate vibrations. The level of fluid in a vessel may be determined by time domain reflectometry as disclosed in U.S. Pat. No. 3,922,914. Also, the constituents of a multi-phased fluid system have been evaluated as disclosed in U.S. Pat. No. 4,786,857.

In addition, time domain reflectometry has been used for optical systems as well. For example, optical time domain reflectometers, such as that disclosed in U.S. Pat. No. 4,960,989, may be used to determine the tip location of a consumable electrode within an electric furnace as disclosed in U.S. Pat. No. 4,843,234. Similarly, optical time domain reflectometry is used in U.S. Pat. No. 5,033,826 to determine which surface of a photographic lens is impairing transmissivity.

It is desirable to provide a method and device using time domain reflectometry to determine the integrity of an implanted electrode to thereby alert the cardiologist or the technician of a potential or existing problem associated with the electrode. As indicated above, time domain reflectometry may be used with both unipolar or bipolar electrodes. The velocity of propagation of any electrode is necessary for time domain reflectometry measurements. Such information could be stored in the implanted device.

It is also desirable to provide a method of analyzing the integrity of the electrode connected to the implantable device. Such analysis could be completed in a programmer such as those used for the analysis of presently available data.

OBJECTS OF THE INVENTION

Accordingly, it is one object of the present invention to provide non-invasive method to establish that an electrode is properly implanted and to determine the integrity of the implanted electrode over a patient's life.

It is another object of the present invention to provide a system whereby the integrity of an implanted electrode may be telemetered to an external analysis unit which may, in turn, provide comparative information to the patient's cardiologist or technician to identify potential or existing problems.

It is still another object of the present invention to provide an electrode integrity testing system in which the test procedure does not interfere with the normal operation of the implanted device.

It is another object of the present invention to provide an integrity testing system which requires little power to operate.

It is still another object of the present invention to provide a testing system which is neither affected by the normal deterioration of the implanted electrode nor affected by physiological changes within the tissue surrounding the electrode.

BRIEF DESCRIPTION OF THE DRAWINGS

FIG. 3 is a representative computer screen list window displaying an index of previous TDR readings which have been stored in the device.

FIG. 4 is a representative computer screen list window displaying a partial index of electrode manufacturers and models, one of which may be selected to provide a set of default electrode, sampling and display options for a particular electrode.

SUMMARY OF THE INVENTION

The invention comprises a device, system and method for testing the integrity of an implantable electrode. The electrical device has a receptacle for an electrode and includes a time domain reflectometer comprising an output signal mechanism operatively connected to the electrode receptacle. The method of analyzing the integrity of an implanted electrode comprises the steps of generating a time domain reflectometer (TDR) reading (output signal) from the electrode, and transmitting the signal to an output device. The output signal may be analyzed to determined whether it varies by a predetermined threshold, or it may be compared to a previously generated signal from the electrode so that differences in the electrical characteristics of the electrode may be identified. The present invention allows a cardiologist or technician to ensure that the electrode is properly implanted and to non-invasively determine the integrity of the electrode over a patient's life.

DETAILED DESCRIPTION

Figure 1:
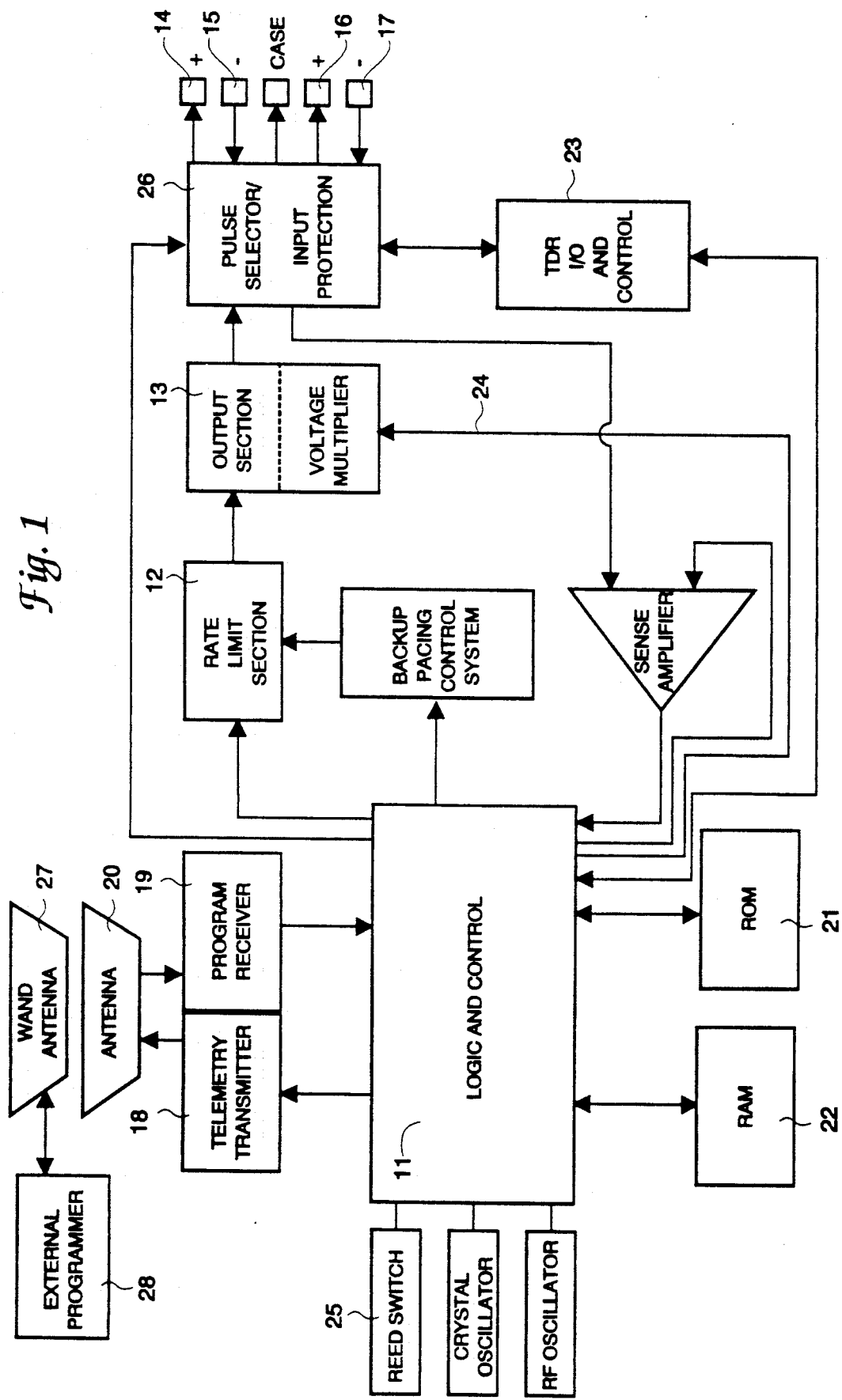
FIG. 1 shows a block diagram of one embodiment of a device of the present invention when used in connection with a programmable cardiac pacemaker.

Referring to FIG. 1, there is shown a representative block diagram of one embodiment of the present invention. In this embodiment, the invention is located in an implantable multi-programmable pacemaker, which includes logic and control unit 11 (which includes a CPU and appropriate software to carry out the functions described herein), rate limit section 12, and output section/voltage multiplier 13. Conventional microcircuitry, and preferably, and application specific integrated circuit, is used to package the TDR and other components in the implantable case. The pacemaker is designed to provide periodic pulse to two implantable pacing electrodes through electrode receiving means, namely connectors 14 and 15, and 16 and 17 respectively. However, the invention may also be used with a device connected to a single electrode. Connected to logic and control unit 11 is a telemetry system comprised of telemetry transmitter 18 and program receiver 19, both of which on connected to common antenna 20. The telemetry system allows the pacemaker to be interrogated to determine its operating conditions after it has been implanted, and also allows the pacemaker to be reprogrammed without surgery. For example, the device can be reprogrammed to generate stimulating pulses on the pacing electrode at set rate, or at a varying rate depending on cardiac activity. Other parameters, such as the pulse width and pulse amplitude can also be specified after the pacemaker has been implanted. These operating parameters are stored in random access memory (RAM) 22, while the control program is stored in read only memory (ROM) 21. Reprogramming is accomplished through the use of an external system programmer 28 having an RF transceiver wand 27, although a convention serial data port with lead connectors extending through the skin of the patient may also be used.

The invention also includes time domain reflectometer (TDR) I/O control 23, which includes the circuitry necessary to generate a TDR pulse on the electrodes and to detect the resulting voltage. A TDR applies a narrow pulse of current (typically by a tunnel diode) to the electrode and monitors the resulting reflected voltage on the electrode over a period of time. A stored reflected voltage waveform comprises a raw TDR reading. If the electrode has a known propagation velocity ($V_p$), the time delay to a particular reflection may be interpreted in distance from the pulse generator. This would include the pacemaker's internal wiring to the pacing electrode connectors, the electrical connection between the connectors and the pacing electrode, and the entire length of the pacing electrode, terminating in the portion placed in heart tissue. The amplitude of the reflected voltage is a function of the electrode impedance and the applied pulse, and therefore can be interpreted in dB, or in rho, which is a function of impedance. Circuitry for time domain reflectometers is well-known and, in isolation, do not form the present invention. In general, a TDR comprises an I/O controller, a digital timebase, an analog timebase, and a pulse generator. As described further below and shown in FIG. 8, the TDR generates a short, square output pulse. After a predetermined amount of time has passed (the TDR base time), the pulse as reflected back by the electrode is monitored. This comprises means for deferring the storing of the TDR signal until the amount time specified by the TDR base time signal has elapsed after the generation of a TDR incident pulse. At a specific time, as determined by the digital timebase, a portion or "slice" of the reflected wave is stored in an analog timebase. This value is then converted to a digital value by an analog to digital converter and stored in memory. The pulse generating-wave storing process is repeated, except that the time period between the pulse generation an when a portion of the reflected wave is stored is increased slightly, causing a different "slice" of the reflected wave to be stored. After a sufficient number of samples (e.g., 256) have been collected, a compilation of the stored waveform readings (a "TDR reading") provides a view of the entire reflected wave. A representative TDR pulse may comprise a 300 mV amplitude into a 50 ohm load, with a 25 microsecond pulse duration, and the reflected rise may be detected in less than 200 picoseconds.

In general, the present invention operates in the following manner. Logic and control 11 is designed to periodically send pacing signals via output line 24 to output section/voltage multiplier 13. Logic and control section 11 is programmed to cause output section/voltage multiplier to generate cardiac stimulating pulses of predetermined amplitude, duration and frequency according to parameters stored in RAM 22. A typical cardiac pacemaker generates stimulating pulses at frequencies of 0.5 to 3 per second, at amplitudes from 2.5 V to 8.5 V, and at durations of 0.15 to 2.3 milliseconds. Accordingly there is a substantial time gap of at least 300 milliseconds between pulses. As a complete TDR pulse and reflection reading time can be accomplished with a pulse repetition rate of 200 microseconds, it is possible to take an entire set of 256 readings in well under 60 milliseconds. Thus a complete TDR reading can be generated between the stimulating pulses periodically provided to the pacing electrode. However, it is also within the scope of the invention to space out the TDR pulses between multiple stimulating pulses.

Prior to implantation of the device in body, the device will be programmed with various default parameters. Conventional pacemakers are programmed, for example to specify the stimulating pulse repetition rate, pulse amplitude, positive and negative sensitivities and control mode. Prior to implantation, one or more pacing electrodes will be selected and connected to pacing leads 14, 15 and 16, 17 of the pacemaker. Each model of electrode has its own characteristics, including a textual model number, polarity, number of filaments, electrical length, physical length, $V_p$ and source resistance. Representative electrode parameters to assist in taking later TDR readings, are shown as electrode menu options 40 in FIG. 2. In addition, each electrode will ideally have a set of default sampling 41 and display 42 options. Preferably, the electrode parameters, sampling and display options may be specified by the electrode manufacturer and used to set default values in the pacemaker prior to implantation. Storing these parameters into the pacemaker is accomplished using conventional telemetry programming equipment with appropriate software to carry out the functions described herein.

To program the default electrode, sampling and display options into the pacemaker, external programmer 28 is first turned on, and the telemetry head of wand antenna 27 is positioned over the pacemaker. The telemetry head generates a magnetic field which activates reed switch 25 inside the pacemaker. This switch causes logic and control unit 11 to activate program receiver 19 and to receive instructions from programmer 28. In one embodiment of the invention, programmer 28 has a touch screen and various options are selected by touching the indicated portion of the screen. The physician will initially step through the prompts displayed on programmer 28 to transmit the desired pacemaker settings (e.g. stimulation rate, pulse amplitudes, sensitivities and mode) into the pacemaker. The physician may then select a TDR option on programmer 28, which will cause programmer 28 permit the TDR parameters to be specified and displayed, such as through the TDR options screen shown in FIG. 2. The physician will initially wish to specify the default TDR values to be stored in the pacemaker. Ideally, programmer 28 will include a database of electrode manufacturers and models, with default electrode, sampling and display options for each electrode model. The database may be periodically updated by programmer 28 manufacturer via a floppy disk with information concerning new electrodes on the market. When the physician first enters the TDR menu, the top "Read Configuration for Pacemaker" option will be highlighted in reverse video. To select a default electrode configuration from the database, the physician presses down arrow 43 to cause the "Select Configuration from Electrode Database" option to be highlighted. The physician then depresses the Select button 50 on the screen. This causes an overlapping window to be displayed on the screen as shown in FIG. 4, displaying a list of electrode manufacturers and model numbers. The physician may repeatedly depress the down arrow until the electrode to be implanted is highlighted, then depress the Select option 50 on the touch screen. This will close the display window, and cause the Electrode, Sampling and Display options to be set to the default values recorded in the database for the particular electrode. While in this window (or any other window which may be opened) at any time prior to depressing the Select option 50, the physician may depress the Escape 47 portion on the screen, which will close the window and cause the display to revert to its previous status. A representative window and set of electrode default information values is shown in FIG. 1. Should the physician desire to change any of the default values, the physician may repeatedly depress the down arrow until the value to be changed is highlighted. The physician may then depress the left 48 and/or right 49 arrows, which will cause the highlighted values to be decremented or incremented, respectively.

After the physician has specified the desired electrode configuration values, the physician may store them in the pacemaker so that they do not have to be reprogrammed each time a TDR reading is taken. This is done by depressing the up or down arrows until the "Store Configuration to Pacemaker" option is selected. The Select button is then depressed, which causes all of the displayed electrode information to be transmitted to the pacemaker by RF transceiver 27 and stored in RAM 22. If the pacemaker provides means for connecting to a second electrode, such as for multiple leads, or includes two leads for single electrode (i.e. a pulse and a ground) then the pacemaker RAM 22 may be configured with sufficient memory to store a separate setting for each electrode or lead. In addition, pulse selector will include switch means for selecting whether the time domain reflectometer is operably connected to the means for connecting the first implantable electrode or the means for connecting to the second implantable electrode. The location for each storage will be designated by the "Electrode No." option in FIG. 2. If a pacemaker having capability for storing only one set of electrode readings receives an instruction and data to store electrode settings for an electrode other than no. 1, the number information may be ignored and the values replaced by the received values.

After this information has been specified, and prior to implantation, the physician may take an initial TDR reading. This is done by using the up and down arrows to highlight the "Obtain TDR Reading" option, the depressing the Select option 50 on the touch screen. This action causes programmer 28 to transmit a command to the pacemaker commanding the pacemaker to take a TDR reading according to the parameters stored in RAM 22.

Figure 8:
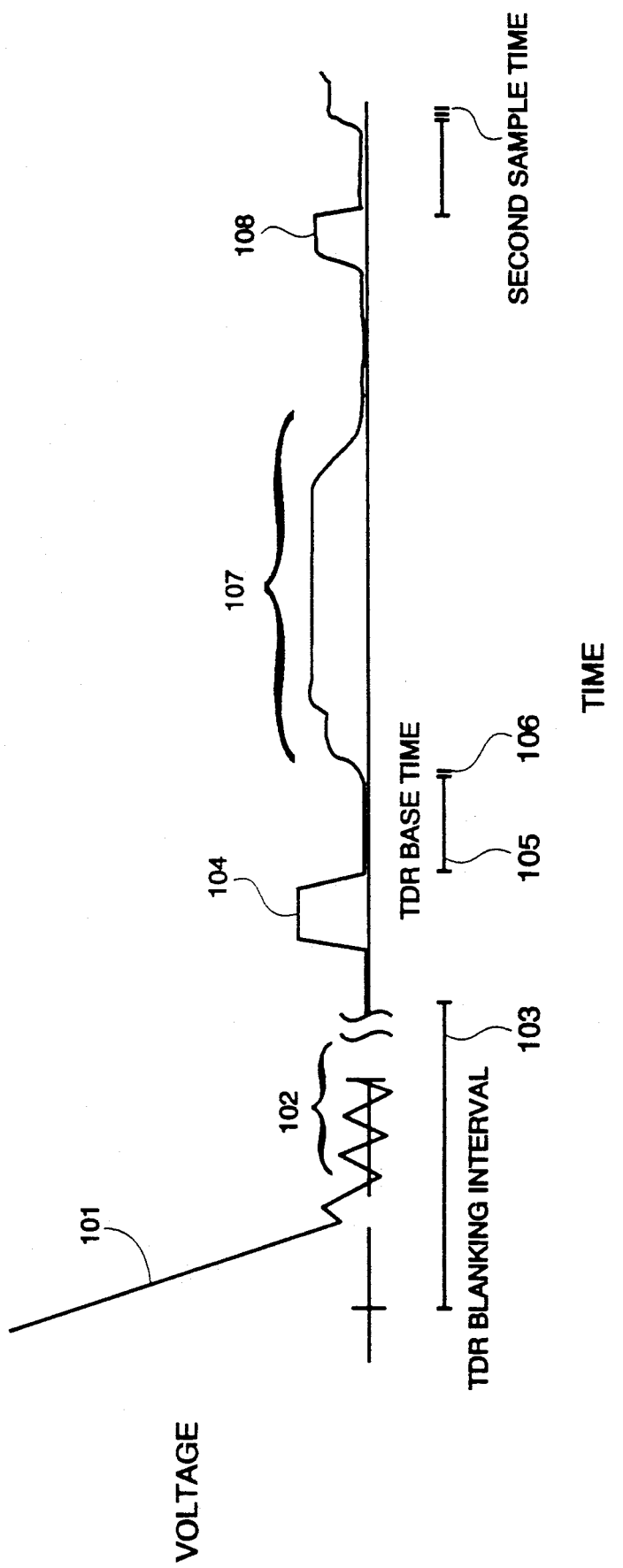
FIG. 8. is a representative time graph showing the trailing end of a stimulating pulse on the electrode, a TDR incident pulse, and reflective pulse.

When the pacemaker receives an instruction to take a TDR reading, the pacemaker waits until no stimulating pulse is present on the electrode. Referring to FIG. 8, normally, if stimulating pulses are being generated on a periodic basis, logic and control unit 11 will wait until the trailing edge of stimulating pulse 101 has been generated. Because stimulating pulse 101 may cause noise to be present on the electrode for a short time period after the pulse is generated, no action is taken during the time previously specified as TDR Blanking Interval 103. This system comprises means for deferring generation of the TDR incident pulse until the amount of time specified by the TDR blanking interval has elapsed after the transmission of a stimulating pulse on the electrode, or the detection of an identified physiological event. For stimulating pulse electrodes, this allows voltage on the electrode to completely drain until the TDR reading process begins. Also, some sensing electrodes, such as those used to monitor heart activity, may have a rhythmic voltage on them generated by an internal organ. Such electrodes are used, for example, to monitor cardiac activity, and logic and control unite 11 section of the pacemaker is capable of determining, at any point in time, the status of the rhythmic activity. For such electrodes, it is desirable to time each TDR reading to being at the same time in the rhythmic cycle so that each TDR reading is taken at the same time of the rhythmic cycle, and therefore less subject to noise. For a cardiac sensing electrode, TDR blanking interval 103 may begin after completing of physiological event such as the atrial beat, as sensed by logic and control 11, and last for 300 milliseconds. After the 300 millisecond blanking interval, the TDR reading (or readings) may be made, as further described below, and the readings may be completed before the ventricular beat begins. This method; in combination of the minimal current needed to generate a TDR incident pulse, minimizes the likelihood of causing an irregular heartbeat. This system constitutes an anti-coincidence detector adapted to prevent a stimulating signal or physiological event from interfering with the incident pulse signal generated by the time domain reflectometer and its reflected wave.

After the TDR blanking interval has passed, logic and control system 11 sends an signal to pulse selector unit 26, which causes the electrode leads to be switched from an electrical connection with output section 13 to the TDR I/O and control section 23. (During normal pacemaker operation, TDR I/O and control 23 is insulated by pulse selector 26 from the stimulating pulses, to minimize the possibility that the relatively large currents and voltages of the stimulating pulses will harm the TDR circuitry.)

Logic and control 11 then sends a signal to TDR I/O and control 23, which comprises means for transmitting an electrical signal to the electrode receiving means, commanding the TDR to generate an incident pulse 104 (see FIG. 8) on the selected electrode lead.

In one embodiment of the invention, logic and control section 11 may include in the signal it sends to TDR I/O 23 a signal representing a impedance through which the TDR pulse should be sent. Ideally, the impedance equals the impedance of the electrode. Accordingly, TDR I/O 23 may include an internal array of source resistors of various impedances through which an incident pulse may be transmitted, and be connected to a multiplexor to select which resistor the pulse should be transmitted. This provides a preferred TDR reflection waveform.

After generation of incident pulse 104, TDR I/O waits the amount of time represented by TDR Base time 105. Normally, this amount of time will be selected to represent the amount of time it will take for a reflected pulse to be detected by TDR I/O 23, and may be on the order of 1-10,000 nanoseconds, depending on the electrical characteristics and length of the electrode. After TDR Base Time 105 passes, the TDR stores analog voltage detected 106 on the electrode in an analog timebase. Voltage 106 represents only a small portion of the entire reflected waveform 107. This analog voltage value is then converted to digital format by an analog-to-digital converter in TDR I/O 23, and then transmitted to logic and control section 11 for storage in output device, such as RAM 22. After a predetermined amount of time, such as 200 microseconds from the initiation of the first incident pulse, TDR I/O 23 generates second TDR pulse 108. The above process is repeated numerous (e.g. 256) times, except the time at which an analog voltage reading is stored in the analog timebase is incremented slightly with each cycle. As a result, RAM 22 has stored in it a raw TDR reading representing the reflected waveform.

After the TDR reading has been generated, logic and control section 11 sends a signal to pulse selector 26 causing the electrode connectors 14, 15 and/or 16,17 to be electrically reconnected to the output section 13, and electrically disconnected from TDR I/O 23. The isolation of TDR I/O 23 from output section 13 by pulse selector 26 guards against any damage to the circuitry of TDR I/O 23 from stimulating pulses generated by output section 13. Thereafter, the generation of stimulating pulses may resume.

If the number of readings averaged parameter is greater than one, then the TDR reading process may be repeated, either immediately, if the time until the next stimulating pulse to be generated is sufficiently long, or else after the next stimulating pulse is generated. Taking multiple TDR readings and averaging them reduces any noise that may be inherent in a single reading. For averaged readings, instead of storing the each set of individual TDR waveform readings to the same RAM address, the digital values may be added to the previously stored values. After the total number of TDR readings specified by the "No. of Readings Averaged" parameter has been completed, the each sum may be divided by the number of readings comprising the sum to obtain a composite reading, namely the average. Alternatively, it is envisioned that merely the raw TDR readings may be transmitted to programmer 28 as described below, and programmer 28 perform the averaging of the readings.

It will be appreciated from the description of the foregoing embodiment that the time domain reflectometer, i.e. the system for generating incident pulses and storing the reflected wave form, comprises a logic and control system as is already found in conventional pacemakers, as well as TDR I/O circuitry.

Figure 7:
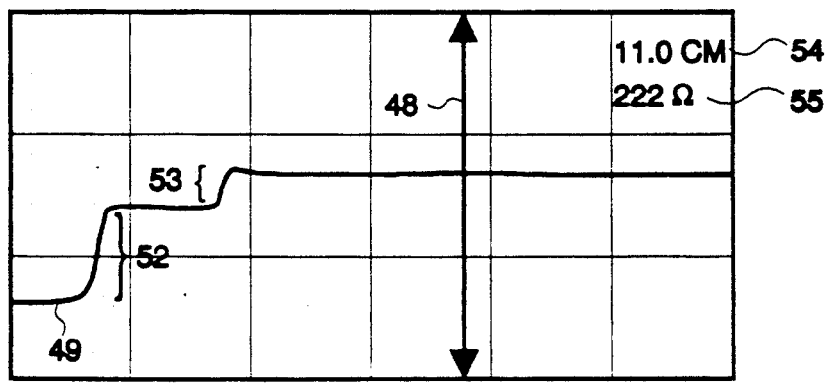
FIG. 7 is a representative graphically displayed TDR reading for an electrode have a short in it.

After the raw or composite TDR reading has been stored in RAM 22, logic and control section 11 transmits the stored raw or composite waveform through TDR reading output signal means, such as transceiver means comprised of telemetry transmitter 18 and antenna 20, to wand 27 of programmer 28. In addition, in the preferred embodiment, logic and control section 11, will also transmit to programmer 28, the stored sampling values used to take the TDR reading to programmer 28. This transmission assures that the correct parameter values may be displayed in association with the TDR reading. Programmer 28 then displays the received TDR reading in graphical form on a monitor (in graphical display window 411) or a printer, or both. Preferably, programmer 28 includes a Print button which when depressed, causes the displayed graph, and current configuration information to be printed. A representative TDR waveform for a working electrode is shown in FIG. 7. The horizontal axis represents the time, or sequential samples of the TDR reading, which can be directly converted into electrode distance if the $V_p$ of the electrode is known. As discussed above, this information may be supplied by the electrode manufacturer or manually programmed into the programmer. With a known $V_p$, the vertical gridlines, or divisions, represent a specific length from the TDR I/O output to the end of the electrode. The vertical axis of the waveform represents millirhos, which is directly convertible into impedance. Thus, a rise in the waveform represents increased resistance along the electrode, while a fall in the waveform represents a short circuit between the electrode and the pacemaker ground.

Accordingly, for the representative waveform shown in FIG. 7, waveform rise 52 represents an increase in resistance, which in this representative case, is attributable to the internal pacemaker wiring connection between the application specific integrated circuit on which pacemaker circuitry is connected and the wires connected to the pacing leads 14, 15, and 16, and 17. Second waveform rise 53 is attributable to the interconnection between electrode receptacle and the electrode plug. Thereafter, the waveform is flat, indicating a constant impedance throughout the length of the electrode, with no breaks or shorts.

Figure 5:
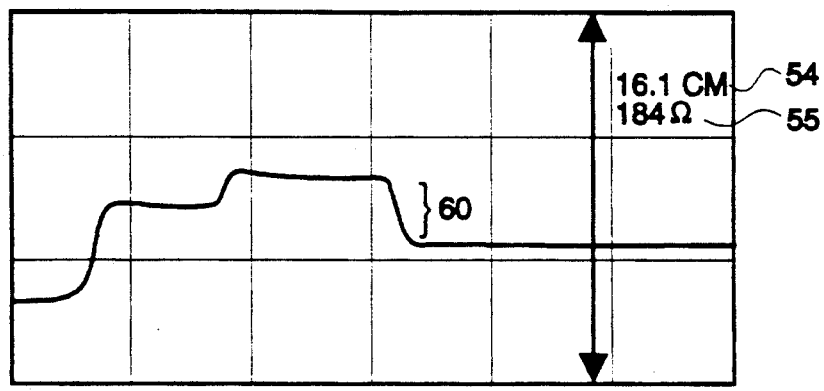
FIG. 5 is a representative graphically displayed baseline TDR reading for an electrode in good condition.

FIG. 5 shows a representative TDR reading in which the electrode has a partial short and is in need of replacement. Such a short may be caused, for example, by defective insulation between the leads of a bipolar electrode, or by the exterior insulation of the electrode becoming worn by, for example, excessive rubbing against a bone, pacemaker case or other structure. The short is evident by waveform fall 60, indicating the impedance of the electrode at that point has fallen.

At anytime while a TDR Reading is displayed, the physician may depress the cursor left 45 or cursor right 46 arrows below the display to cause graphical cursor 48 to move left or right. At the point where cursor 48 intersects waveform 49, the distance of the electrode circuit and impedance of the waveform are shown in displays 54 and 55. Thus, cursor 48 and displays 54 and 55 comprise means for superimposing a distance scale measurement corresponding to the length of the implanted electrode on the graphical display.

Figure 2:
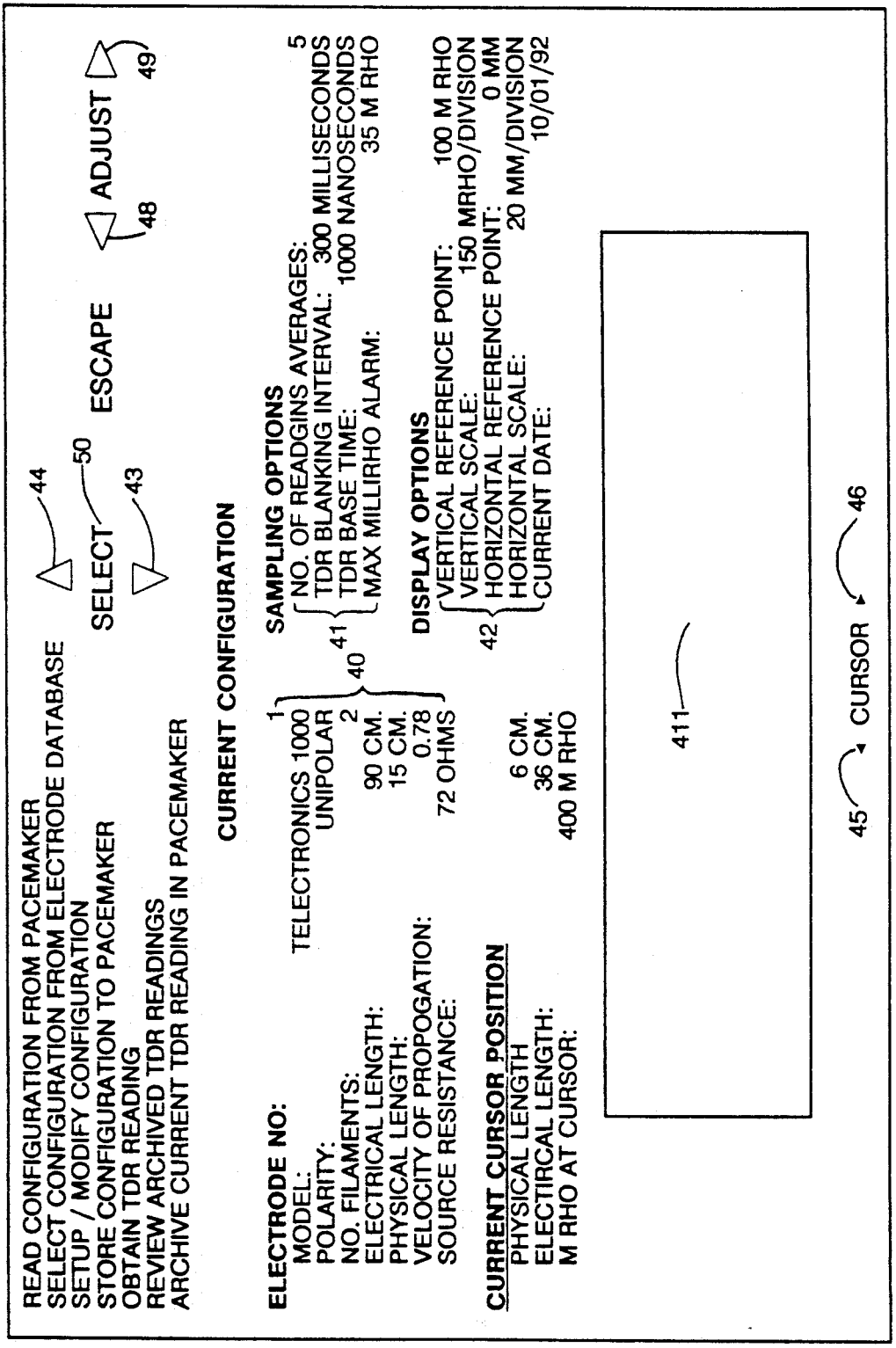
FIG. 2 a representative computer touch screen user interface for configuring and testing an implantable electrode according to the invention.

After the physician has obtained and displayed the composite TDR reading, the reading may be transmitted back to the pacemaker and stored in RAM 22, which comprises means for storing multiple TDR output signals. As shown in FIG. 2, this may be done by depressing the down arrow until the "Archive Current TDR Reading in Pacemaker" menu option is highlighted. The Select button is then depressed. This causes programmer 28 display a dialog box on the screen in which the physician may type a short descriptive summary of the reading using a keyboard connected to programmer 28, such as "Pre-implant readings w/Technitronics 1000", and in which the physician may enter his or her name. After this option information has been entered, the Select button is again depressed, causing programmer 28 to transmit the TDR waveform, along with the Sampling Options, Display Options and textual information (including the date, which comprises a means for associating each stored output signal with a time reference indicating when the output signal is generated) through wand antenna 27 to antenna 20 of the pacemaker, accompanied by a command instructing the pacemaker logic and control 11 to store the information in RAM 22. This stored reading may be used as a baseline TDR reading against which future TDR readings may be compared to assist in evaluating electrode integrity. In one embodiment, RAM 22 has sufficient capacity to store up to 512 TDR readings and associated information. Logic and control 11 stores in RAM 22 an incremental counter indicating the total number of readings that have been stored in RAM 22 and the address of the next subsequent reading to be stored.

Assuming the initial TDR reading is acceptable, the physician may proceed with implantation of the pacemaker and electrode. Following implantation, but prior to closing the surgical incision in the patient, the physician may take a second TDR reading to ensure that no damage to the pacemaker or electrode occurred during implantation. Assuming the TDR reading is acceptable, the physician may close the incision.

Following implantation, the patient can be expected to have numerous follow-up visits with the physician, during which the integrity of the implanted electrode may be evaluated. This may be done using the same programmer 28 described above. After the programmer is turned on, wand 27 is positioned over the patient's pacemaker, and the TDR option is selected, the screen shown in FIG. 2 may appear. The physician choose to first retrieve a copy of the archived TDR reading from when the electrode was first implanted. This may be done by using up 44 and down 43 arrows to highlight the "Review Archived TDR Readings" option, and depressing Select. This will cause programmer 28 to send a signal to the pacemaker instructing logic and control section 11 to transmit the archive number, date, comment and physician portions of each archived TDR reading to the programmer. An archived TDR display window, as shown in FIG. 3 is then displayed. Using up 44 and down 43 arrows, the physician may highlight an archived TDR reading, which will normally be the baseline reading or first reading archived after implantation. Depressing the Select portion of the screen causes programmer 28 close the widow and to command the pacemaker to transmit the selected archived TDR reading (including the electrode, sampling and display options) to the programmer, where they are displayed. The physician may then depress the up arrow to highlight the "Obtain TDR Reading" menu option, then press Select 50. This will cause a TDR reading to be generated as described above, and superimposed over the archived TDR reading.

By highlighting and adjusting the "Max MIllirho Alarm" option, the physician may specify a millirho value (predetermined threshold) by which, if a TDR reading deviates in a relevant portion, an indicating output warning signal, such as a flashing light, buzzer, or "DEFECTIVE" screen display is generated. High and low limits from the electrode portion of the display waveform may be represented as horizontal lines on the graphical display. Specifically, minimum warning line 64 and maximum warning line 65 as shown in FIG. 67 define the boundaries in which the entire electrode portion of the waveform is expected to fall. If a waveform deviates from these limits, DEFECTIVE legend 66 may be displayed on the screen, preferably in a highly contrasting color and accompanied by an audible alarm.

Figure 6:
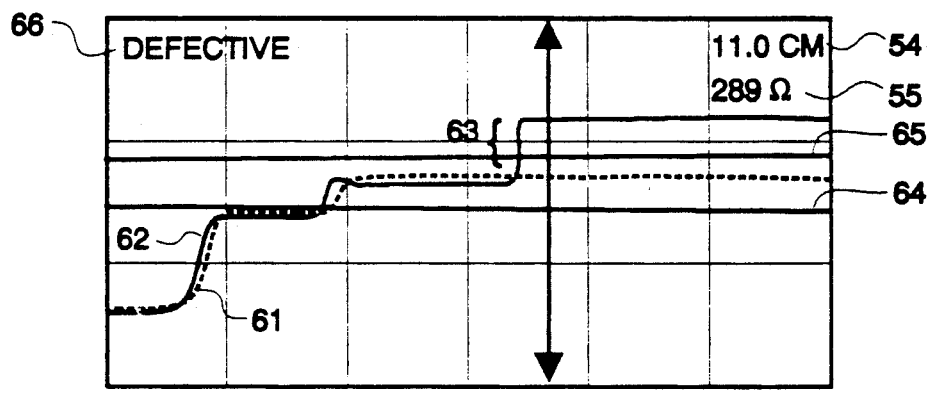
FIG. 6 is a representative graphically displayed baseline TDR reading having superimposed over it a more recent TDR reading for the same electrode showing that a break has occurred in the electrode and that the electrode is now defective.

FIG. 6 shows a representative superimposed TDR reading, in which archived reading 61 shows an electrode in good condition, while current reading 62 shows that the electrode has broken. Specifically, reading 62 includes waveform rise 63, indicating that the impedance of the electrode has risen. This may be caused by, for example, a filament becoming cracked or completely severed. Because current reading 62 exceeds maximum alarm level 65, DEFECTIVE legend 66 is displayed on the screen, alerting the physician that the electrode may be defective.

The Current Configuration parameters 40, 41 and 42 shown in FIG. 2, as mentioned above, may be adjusted. With regard to Display Options 42, these parameters effect how a particular TDR reading is displayed on the screen. In particular, different electrodes from different manufacturers and for different purposes will generate TDR readings have different impedance baselines and lengths. In order to scale a TDR reading on the graphical display, the Vertical and Horizontal reference points and scales may be adjusted. These values will also be stored along with an archived TDR reading so that when the reading is retrieved, it will be initially displayed using the same viewing parameters as when it was stored.

It will be appreciated to those of skill in the art that may changes could be made in the foregoing representative embodiment without departing from the spirit and scope of the invention. For example, the present invention may be used with virtually any type of implantable electrode, such as ventricular, rate sensing, morphology, high voltage, mapping, sensor, temporary, ablation and angio/artheretomy electrodes. The invention may also be used in connection with wires used in connection with devices such as implanted insulin pumps, and such wires are within the scope of the term "electrode" as used herein and in the claims. In addition, in instances where a tube or stint is implanted in a patient, a tube configured with an embedded electrical conductor running the length of the tube and connectable to a TDR, and which will break if the tube breaks, is also included within the definition of an electrode as used herein.

It will also be appreciated that although the in the embodiment described above a TDR reading is output through RAM and an RF antenna, other transceiver or output means are within the spirit and scope of the invention. For example, virtually any other electromagnetic wave communication means may be used, at any desired frequency, including optical frequencies, or wire leads may be used to transmit a TDR reading. Moreover, the TDR reading described above is obtained by generating multiple incident pulses and storing a small portion of each reflected pulse. It is contemplated that with the development of faster electronic and CPU circuitry, that a TDR reading may possibly be generated by storing the reflected wave from a single incident pulse, and such systems included within the definition of a TDR. It will also be appreciated that in the embodiment described above, a user-selected number of multiple raw TDR readings may be averaged to produce a composite reading to eliminate noise associated with individual readings. The averaging function could easily be transferred from the internal implantable device to external programmer 28. Moreover, other manipulations of raw TDR readings, such as by averaging multiple readings, would not necessarily alter their definition as being a TDR reading. Other functions contemplated to be performed by the pacemaker could also be performed by external programmer 28. For example, the storage of TDR readings could be performed on external programmer 28, and optionally, may be indexed by a unique key, such as patient social security number or pacemaker serial number, to distinguish between stored readings from different patients. Also, graphical display of programmer 28 may include means for displaying the amplitude differential between the incident pulse and a selected portion of a TDR reading.

What is claimed is:

1. An electrical device implantable in a body, the device comprising means for receiving a first electrode, comprising:
   time domain reflectometer means operatively connected to the means for receiving the electrode, the time domain reflectometer means comprising output signal means.

2. The device of claim 1 wherein the device comprises a pacemaker.

3. The device of claim 1 wherein the device comprises an automatic implantable cardioverter defibrillator.

4. The device of claim 1 wherein the output signal of the means comprises a single TDR reading from the time domain reflectometer.

5. The device of claim 1 wherein the output signal of the device comprises a composite reading from multiple readings from the time domain reflectometer.

6. The device of claim 5, wherein the composite reading from multiple readings comprises an average of the multiple readings based upon a user-designated number of TDR readings from the time domain reflectometer.

7. The device of claim 1 further comprising:
   means for storing multiple output signal means.

8. The device of claim 7 further comprising:
   means for associating each stored output signal with a time reference indicating when the output signal is generated.

9. The device of claim 7 further comprising:
   means for transmitting a specified stored output signal through the output signal means.

10. The device of claim 1 wherein the time domain reflectometer means comprises means for transmitting an electrical signal to the electrode receiving means, and
    wherein the device further comprises
    an anti-coincidence detector adapted to prevent a signal generated by the transmitting means from interfering with the signal generated by the time domain reflectometer.

11. The device of claim 1 further comprising:
    means for actuating the time domain reflectometer to generate an output signal, the actuating means comprising an electromagnetic wave receiver.

12. The device of claim 1 further comprising:
    means for transmitting an output signal generated by the time domain reflectometer, the transmitting means comprising an electromagnetic wave transmitter.

13. The device of claim 1, wherein the time domain reflectometer further comprises:
    a pulse generator, and
    an array of selectable source resistors through which a pulse generated by the pulse generator may be transmitted.

14. The device of claim 1, wherein the device further comprises:
    means for receiving a TDR blanking interval signal to the time domain reflectometer, and
    means for deferring generation of a TDR pulse until the amount of time specified by the TDR blanking interval has elapsed after the transmission of a stimulating pulse, or occurance of an identified physiological event, on the electrode.

15. The device of claim 1, wherein the device further comprises:
    means for receiving a TDR base time signal to the time domain reflectometer, and
    means for deferring storing of the reflected TDR incident pulse until the amount time specified by the TDR base time signal has elapsed after the generation of a TDR pulse.

16. The device of claim 1, wherein the device further comprises:
    means for connecting the device to a second implantable electrode, and
    switch means for selecting whether the time domain reflectometer is operably connected to the means for connecting the first implantable electrode or the means for connecting to the second implantable electrode.

17. The device of claim 1, wherein the device further comprises:
    means for storing information regarding an electrode connectable to the device, and
    means for transmitting the stored information through the output signal means.

18. A system for displaying a time domain reflectometer output signal, comprising:
    a device of claim 10, and
    a graphical display means operatively connected to a receiving means for receiving a transmitted output signal from the device of claim 8.

19. A method of analyzing the integrity of an electrode implanted in a body comprising the steps of:
    generating a first time domain reflectometer (TDR) reading from the implanted electrode, and transmitting the generated TDR reading to an output means.

20. The method of claim 19, further comprising the step of:
   providing a reference time domain reflectometer reading, and
   comparing the first and reference time domain reflectometer readings and
   generating an indicating output based on whether the first and reference output signals vary by a predefined threshold.

21. The method of claim 19 wherein the implanted electrode comprises a pacemaker electrode.

22. The method of claim 19 wherein the implanted electrode comprises an automatic implantable cardioverter defibrillator electrode.

23. The method of claim 19 further comprising the step of
   generating multiple output signals from the time domain reflectometer, and
   combining the multiple output signals to form a composite output signal.

24. The method of claim 23, wherein the composite reading from multiple readings comprises an average of the multiple readings based upon a user-designated number of TDR readings from the time domain reflectometer.

25. The method of claim 19, further comprising the step of:
   selecting a source resistance for the incident pulse generated by the time domain reflectometer.

26. The method of claim 19, further comprising the step of: storing the generated TDR reading.

27. The method of claim 26, further comprising the step of:
   associating each stored output signal with a time reference indicating when the TDR reading is generated.

28. The method of claim 19, further comprising the step of:
   transmitting a previously stored output signal through the output means.

29. The method of claim 19, wherein the output means comprises an electromagnetic wave receiver.

30. The method of claim 19, further comprising the steps of:
   providing a TDR blanking interval signal, and
   deferring generation of a TDR pulse until the amount of time specified by the TDR blanking interval has elapsed after the transmission of a stimulating pulse, or the occurrence of an identified physiological event, on the electrode.

31. The method of claim 19, further comprising the steps of:
   providing a TDR base time signal to the time domain reflectometer, and
   deferring the storing of the reflected TDR incident pulse until the amount time specified by the TDR base time signal has elapsed after the generation of a TDR pulse.

32. The method of claim 19, further comprising the steps of:
   graphically displaying the generated TDR reading.

33. The method of claim 32 further comprising the steps of:
   providing a reference output signal, and
   superimposing the reference output signal on the graphically displayed generated output signal.

34. The method of claim 32 further wherein the generated output signal is displayed on a screen monitor.

35. The method of claim 32 further wherein the generated output signal is displayed on a printer.

36. The method of claim 19, further comprising the steps of:
   selecting a portion of the generated TDR reading, and
   graphically displaying the selected portion of the TDR reading.

37. A system for testing the integrity of an implanted electrode, the implanted electrode being connected to device comprising a transceiver means and a time domain reflectometer connected to the electrode, the time domain reflectometer being capable of generating an output signal, comprising:
   means for transmitting a signal to the device transceiver means commanding the time domain reflectometer to generate a first TDR reading from the implanted electrode and transmit TDR reading through the transceiver, and
   means for receiving the transmitted first TDR reading.

38. The system of claim 37, wherein the system further comprises:
   means for storing multiple received TDR readings,
   means for comparing at least two of the transmitted TDR readings, and
   means for indicating whether the compared TDR readings vary by a predefined threshold.

39. The system of claim 37, wherein the system further comprises:
   means for graphically displaying the received first TDR reading.

40. The system of claim 39, wherein the system further comprises:
   means for selecting a portion of the first TDR reading to be graphically displayed.

41. The system of claim 39, wherein:
   the first TDR reading is graphically displayed using an axis indicating the time/distance of the output signal, and
   wherein the system further comprises means for selecting the time/distance scale at which the first TDR reading is graphically displayed.

42. The system of claim 39, wherein the system further comprises means for superimposing a distance scale measurement corresponding to the length of the implanted electrode on the graphical display.

43. The system of claim 37, wherein the system further comprises:
   means for storing a second TDR reading and graphically displaying it superimposed over the first TDR reading.

44. The system of claim 37, wherein the system further comprises:
   means for storing a second TDR reading,
   means for comparing the first and second TDR readings, and
   means for indicating whether the compared TDR readings vary by a predefined threshold.

45. The system of claim 37, wherein the system further comprises:
   means for adjusting the a vertical reference point for the graphical display.

46. The system of claim 37, wherein the system further comprises means for adjusting the vertical sensitivity of the graphical display.

47. The system of claim 37, wherein the graphical display means comprises a screen monitor.

48. The system of claim 37, wherein the graphical display means comprises a printer.

49. The system of claim 37, wherein the device comprises means for generating the first TDR reading by forming a composite reading from multiple TDR readings.

50. The system of claim 49 wherein the system further comprises:
means for transmitting a signal to the device transceiver means indicating the number of TDR readings to use to form the composite signal.

51. The system of claim 37, wherein the system further comprises:
means for storing multiple received TDR readings,
means for generating a TDR reading comprising a composite of individual TDR readings.

52. The device of claim 51, wherein the composite TDR reading comprises an average of the multiple readings based upon a user designated number of readings from the time domain reflectometer.

53. The system of claim 37, wherein the time domain reflectometer further comprises an incident pulse generator, and wherein the system further comprises:
means for selecting a value indicating the source resistance of an incident pulse to be generated by the time domain reflectometer, and
means for transmitting the selected value to the device.

54. The system of claim 37, wherein the system further comprises:
means for specifying a propagation velocity factor for the first TDR reading.

55. The system of claim 37, wherein the system further comprises:
means for selecting a set of properties for the implanted electrode from a database of electrode properties, and
means for displaying at least one of the selected properties.

56. The system of claim 37, wherein the system further comprises:
means for specifying a TDR blanking interval for a TDR reading to be made by the time domain reflectometer of the implanted device, and
means for transmitting the specified TDR blanking interval to the transceiver means.

57. The system of claim 37, wherein the system further comprises:
means for specifying a TDR base time for a TDR reading to be made by the time domain reflectometer, and
means for transmitting the specified TDR base time to the transceiver means.

58. The system of claim 37, wherein the transceiver means comprises and RF transceiver.

59. The system of claim 37, wherein the transceiver means comprises a serial data port.

60. The system of claim 37, wherein the device comprises data storage means and the system further comprises:
means for transmitting an instruction to the device commanding the device to store a TDR reading.

61. The system of claim 37, wherein the device comprises data storage means and the system further comprises:
means for transmitting an instruction to the device commanding the device transmit to the system a previously stored TDR reading.

62. The system of claim 37, wherein the system further comprises:
means for displaying the amplitude differential between the incident pulse and a selected portion of the first TDR reading.

63. The system of claim 37, wherein the device is connected to a plurality of implanted electrodes and includes switch means for selecting which of the implantable electrodes the time domain reflectometer is connected to, further comprising:
means for commanding the device for operably connect the time domain reflectometer to a designated implanted electrode.

64. The system of claim 37, further comprising:
means for commanding the device for operably connected to the time domain reflectometer to transmit stored information regarding an electrode connected to the device to the system.

* * * * *